United States Patent

Stubbs et al.

(10) Patent No.: US 7,091,317 B2
(45) Date of Patent: Aug. 15, 2006

(54) FLUORESCENT PROTEINS

(75) Inventors: Simon Lawrence John Stubbs, Amersham (GB); Anne Elizabeth Jones, Amersham (GB); Nigel Paul Michael, Amersham (GB); Nicholas Thomas, Amersham (GB)

(73) Assignee: GE Healthcare Limited, Amersham (GB)

( * ) Notice: Subject to any disclaimer, the term of this patent is extended or adjusted under 35 U.S.C. 154(b) by 155 days.

(21) Appl. No.: 10/757,624

(22) Filed: Jan. 14, 2004

(65) Prior Publication Data

US 2004/0138420 A1    Jul. 15, 2004

Related U.S. Application Data

(62) Division of application No. 09/967,301, filed on Sep. 28, 2001, now Pat. No. 6,919,186.

(30) Foreign Application Priority Data

Apr. 23, 2001  (GB) ................................. 0109858.1

(51) Int. Cl.
    *C07K 1/00*  (2006.01)
(52) U.S. Cl. ...................... 530/350; 435/69.1; 435/7.1; 435/320.1; 435/252; 514/2; 536/23.1
(58) Field of Classification Search ................ 530/350; 435/7.1, 69.1, 320.1, 252; 536/23.1; 514/2, 514/12
See application file for complete search history.

(56) References Cited

U.S. PATENT DOCUMENTS

| | | | |
|---|---|---|---|
| 5,491,084 A | 2/1996 | Chalfie et al. | |
| 5,804,387 A | 9/1998 | Cormack et al. | 435/6 |
| 6,027,881 A | 2/2000 | Pavlakis et al. | 435/6 |
| 6,054,321 A | 4/2000 | Tsien et al. | 436/86 |
| 6,077,707 A | 6/2000 | Tsien et al. | 435/32 |
| 6,150,176 A | 11/2000 | Tsien et al. | 436/86 |
| 6,172,188 B1 | 1/2001 | Thastrup et al. | |
| 6,194,548 B1 | 2/2001 | Osumi et al. | 530/350 |
| 6,780,975 B1 * | 8/2004 | Tsien et al. | 530/350 |

FOREIGN PATENT DOCUMENTS

| | | |
|---|---|---|
| WO | WO96/23810 | 8/1996 |
| WO | WO96/27675 | 9/1996 |
| WO | WO97/42320 | 11/1997 |
| WO | WO00/08054 | 2/2000 |
| WO | WO01/98338 | 12/2001 |

OTHER PUBLICATIONS

B. Cormack, et al. "FACS-optimized mutants of the green fluorescent protein (GFP)" Gene, 173 (1996) pp. 33-38.
C. Reichel, et al. "Enhanced green fluorescence by the expression of an *Aequorea victoria* green fluorescent protein mutant in mono- and dicotyledonous plant cells" Proc. Natl. Acad. Sci. USA vol. 93, Jun. 1996 pp. 5888-5893.
K. Brejc, et al. "Structural basis for dual excitation and photoisomerization of the *Aequorea victoria* green fluorescent protein" Proc. Natl. Acad. Sci. USA vol. 94, Mar. 1997 pp. 2306-2311.
T. Yang, et al. "Improved Fluorescence and Dual Color Detection with Enhanced Blue and Green Variants of the Green Fluorescent Protein" The Journal of Biological Chemistry vol. 273, No. 14, Apr. 3, 1998 pp. 8212-8216.
M. Chalfie, et al. "Green Fluorescent Protein as a Marker for Gene Expression" Science, vol. 263, Feb. 11, 1994 pp. 802-805.
M. Chalfie "Green Fluorescent Proteins" Photochemistry and Photobiology, vol. 62, No. 4, 1995 pp. 651-656.
R. Heim, et al. "Wavelength Mutations and Posttranslational Autoxidation of Green Fluorescent Proteins" Natl. Acad. Sci., vol. 91, Dec. 1994 pp. 12501-12504.
A. Crameri, et al. "Improved Green Fluorescent Protein by Molecular Evolution Using DNA Shuffling" Nature Biotechnology, vol. 14, 1996 pp. 315-319.
T. Ehrig, et al. "Green-Fluorescent Protein Mutants with Altered Fluorescence Excitation Spectra" Federation of European Biochemical Societies Letters, 367, 1995 pp. 163-166.
R. Heim, et al. "Improved Green Fluorescence" Nature, vol. 373, Feb. 23, 1995 pp. 663-664.

* cited by examiner

*Primary Examiner*—Kathleen M. Kerr
*Assistant Examiner*—Hope Robinson
(74) *Attorney, Agent, or Firm*—Yonggang Ji; Royal N. Ronning, Jr.

(57) ABSTRACT

The present invention provides novel engineered derivatives of green fluorescent protein (GFP) which have an amino acid sequence which is modified by amino acid substitution compared with the amino acid sequence of wild type Green Fluorescent Protein. The modified GFPs exhibit enhanced fluorescence relative to wtGFP when expressed in non-homologous cells at temperatures above 30° C., and when excited at about 490 nm compared to the parent proteins, i.e. wtGFP. An example of a preferred protein is F64L-S175G-E222G-GFP. The modified GFPs provide a means for detecting GFP reporters in mammalian cells at lower levels of expression and/or increased sensitivity relative to wtGFP. This greatly improves the usefulness of fluorescent proteins in studying cellular functions in living cells.

9 Claims, 7 Drawing Sheets

Nucleotide Sequence of wtGFP (Chalfie et al, Science, (1994), 263, 802-5):
SEQ ID NO:1

```
atg agt aaa gga gaa gaa ctt ttc act gga gtt gtc cca att ctt gtt      48 gaa tta gat ggt gat gtt aat ggg cac aaa ttt tct gtc agt gga gag      96 ggt gaa ggt gat gca aca tac gga aaa ctt acc ctt aaa ttt att tgc     144 act act gga aaa cta cct gtt cca tgg cca aca ctt gtc act act ttc     192 tct tat ggt gtt caa tgc ttt tca aga tac cca gat cat atg aaa cgg     240 cat gac ttt ttc aag agt gcc atg ccc gaa ggt tat gta cag gaa aga     288 act ata ttt ttc aaa gat gac ggg aac tac aag aca cgt gct gaa gtc     336 aag ttt gaa ggt gat acc ctt gtt aat aga atc gag tta aaa ggt att     384 gat ttt aaa gaa gat gga aac att ctt gga cac aaa ttg gaa tac aac     432 tat aac tca cac aat gta tac atc atg gca gac aaa caa aag aat gga     480 atc aaa gtt aac ttc aaa att aga cac aac att gaa gat gga agc gtt     528 caa cta gca gac cat tat caa caa aat act cca att ggc gat ggc cct     576 gtc ctt tta cca gac aac cat tac ctg tcc aca caa tct gcc ctt tcg     624 aaa gat ccc aac gaa aag aga gac cac atg gtc ctt ctt gag ttt gta     672 aca gct gct ggg att aca cat ggc atg gat gaa cta tac aaa tag        717
```

FIGURE 1

Amino Acid Sequence of wtGFP (Chalfie et al, Science, (1994), 263, 802-5

SEQ ID NO:2

```
Met Ser Lys Gly Glu Glu Leu Phe Thr Gly Val Val Pro Ile Leu Val
 1           5                   10                  15
Glu Leu Asp Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
            35                  40                  45
Thr Thr Gly Lys Leu Pro Val Pro Trp Pro Thr Leu Val Thr Thr Phe
     50                  55                  60
Ser Tyr Gly Val Gln Cys Phe Ser Arg Tyr Pro Asp His Met Lys Arg
 65                  70                  75                  80
His Asp Phe Phe Lys Ser Ala Met Pro Glu Gly Tyr Val Gln Glu Arg
            85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Leu Glu Tyr Asn
            130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
            195                 200                 205
Lys Asp Pro Asn Glu Lys Arg Asp His Met Val Leu Leu Glu Phe Val
            210                 215                 220
Thr Ala Ala Gly Ile Thr His Gly Met Asp Glu Leu Tyr Lys
225                 230                 235
```

FIGURE 2

Predicted Amino Acid Sequence of F64L-S175G-E222G-GFP:

SEQ ID NO:3

```
Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Ser Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Gly Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Gly Phe Val
    210                 215                 220
Thr Ala Ala Gly Ile Thr His Gly Met Asp Glu Leu Tyr Lys
225                 230                 235
```

FIGURE 3

Predicted Amino Acid Sequence of F64L-S65T-S175G-GFP:

SEQ ID NO:4

```
Met Ser Lys Gly Glu Glu Leu Phe Thr Gly Val Val Pro Ile Leu Val
1               5               10                  15
Glu Leu Asp Gly Asp Val Asn Gly His Lys Phe Ser Val Ser Gly Glu
            20              25              30
Gly Glu Gly Asp Ala Thr Tyr Gly Lys Leu Thr Leu Lys Phe Ile Cys
        35              40              45
Thr Thr Gly Lys Leu Pro Val Pro Trp Pro Thr Leu Val Thr Thr Leu
    50              55              60
Thr Tyr Gly Val Gln Cys Phe Ser Arg Tyr Pro Asp His Met Lys Arg
65              70              75                  80
His Asp Phe Phe Lys Ser Ala Met Pro Glu Gly Tyr Val Gln Glu Arg
            85              90              95
Thr Ile Phe Phe Lys Asp Asp Gly Asn Tyr Lys Thr Arg Ala Glu Val
            100             105             110
Lys Phe Glu Gly Asp Thr Leu Val Asn Arg Ile Glu Leu Lys Gly Ile
        115             120             125
Asp Phe Lys Glu Asp Gly Asn Ile Leu Gly His Lys Leu Glu Tyr Asn
    130             135             140
Tyr Asn Ser His Asn Val Tyr Ile Met Ala Asp Lys Gln Lys Asn Gly
145             150             155                 160
Ile Lys Val Asn Phe Lys Ile Arg His Asn Ile Glu Asp Gly Gly Val
            165             170             175
Gln Leu Ala Asp His Tyr Gln Gln Asn Thr Pro Ile Gly Asp Gly Pro
            180             185             190
Val Leu Leu Pro Asp Asn His Tyr Leu Ser Thr Gln Ser Ala Leu Ser
        195             200             205
Lys Asp Pro Asn Glu Lys Arg Asp His Met Val Leu Leu Glu Phe Val
    210             215             220
Thr Ala Ala Gly Ile Thr His Gly Met Asp Glu Leu Tyr Lys
225             230             235
```

FIGURE 4

SEQUENCE LISTING

<160> NUMBER OF SEQ ID NOS: 19

<210> SEQ ID NO 1
<211> LENGTH: 717
<212> TYPE: DNA
<213> ORGANISM: Aequorea victoria

<400> SEQUENCE: 1

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcaagat acccagatca tatgaaacgg   240
catgactttt tcaagagtgc catgcccgaa ggttatgtac aggaaagaac tatattttc    300 aaagatgacg ggaactacaa gacacgtgct gaagtcaagt ttgaaggtga taccctggtt    360
aatagaatcg agttaaaagg tattgatttt aaagaagatg gaaacattct tggacacaaa    420
ttggaataca actataactc acacaatgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaatag       717
```

<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 3
<211> LENGTH: 238
<212> TYPE: PRT
<213> ORGANISM: Artificial Sequence
<220> FEATURE:
<223> OTHER INFORMATION: synthetic protein

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Arg
65                  70                  75                  80

```
His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Gly Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Gly Phe Val
            210                 215                 220

Thr Ala Ala Gly Ile Thr His Gly Met Asp Glu Leu Tyr Lys
225                 230                 235
```

```
<210> SEQ ID NO 4
<211> LENGTH: 238
<212> TYPE: PRT
<213> ORGANISM: Artificial Sequence
<220> FEATURE:
<223> OTHER INFORMATION: synthetic protein

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
            85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Gly Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205
```

-continued

```
Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 5
ggtacgggcc gccaccatga gtaaaggaga agaactttc ac                     42

<210> SEQ ID NO 6
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 6
ggtacgggtt aaccggtttt gtatagttca tccatg                           36

<210> SEQ ID NO 7
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 7
ggtacgggcc gccaccatgg gatccaaagg agaagaactt ttcac                 45

<210> SEQ ID NO 8
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 8
ccaacacttg tcactactct ctcttatggt gttcaat                          37

<210> SEQ ID NO 9
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 9
attgaacacc ataagagaga gtagtgacaa gtgttgg                          37

<210> SEQ ID NO 10
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 10
ccaacacttg tcactactct cacctatggt gttcaatgct tttca                 45
```

```
<210> SEQ ID NO 11
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 11
tgaaaagcat tgaacaccat aggtgagagt agtgacaagt gttgg            45

<210> SEQ ID NO 12
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 12
gacaaacaaa agaatggaat caaagccaac ttcaaaatta gacac            45

<210> SEQ ID NO 13
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 13
gtgtctaatt ttgaagttgg ctttgattcc attcttttgt ttgtc            45

<210> SEQ ID NO 14
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 14
caacattgaa gatggaggcg ttcaactagc agacc                       35

<210> SEQ ID NO 15
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 15
ggtctgctag ttgaacgcct ccatcttcaa tgttg                       35

<210> SEQ ID NO 16
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 16
ccacatggtc cttcttggct ttgtaacagc tgctgg                      36

<210> SEQ ID NO 17
<211> LENGTH: 36
<212> TYPE: DNA
<213> ORGANISM: Artificial Sequence
<220> FEATURE:
<223> OTHER INFORMATION: synthetic oligonucleotide
```

```
<400> SEQUENCE: 17
ccagcagctg ttacaaagcc aagaaggacc atgtgg                      36

<210> SEQ ID NO 18
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 18
ttttgaagct tggagctgat ctgactcagc agg                         33

<210> SEQ ID NO 19
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 19
ttttactcga gatggacgaa ctgttccccc tca                         33
```

FLUORESCENT PROTEINS

The present application is a divisional of U.S. patent application Ser. No. 09/967,301 filed Sep. 28, 2001, now U.S. Pat. No. 6,919,186, which claims priority to Application No. GB 0109858.1 filed on Apr. 23, 2001, the entire disclosures of which are hereby incorporated by reference.

FIELD OF THE INVENTION

The present invention relates to novel variants of the fluorescent protein GFP having improved fluorescence properties.

BACKGROUND OF THE INVENTION

The use of Green Fluorescent Protein (GFP) derived from *Aequorea Victoria* has revolutionised research into many cellular and molecular-biological processes. GFP allows researchers to label proteins within cells with an intrinsic fluor, so obviating the requirement to perform chemical labelling of proteins, and allowing development of assays of biological processes in intact living cells.

U.S. Pat. No. 5,491,084 describes the use of GFP as a biological reporter. Early applications of GFP as a biological reporter (Chalfie et al. Science, (1994), 263, 802–5; Chalfie, et al, Photochem.Photobiol., (1995), 62(4), 651–6) used wild type (native) GFP (wtGFP), but these studies quickly demonstrated two areas of deficiency of wtGFP as a reporter for use in mammalian cells. Firstly, the protein being derived from a poikilothermic marine organism does not undergo protein folding efficiently when expressed in mammalian cells cultured at 37° C., resulting in weak fluorescence. Secondly, the spectral characteristics of the wtGFP are not ideally suited to use as a cellular reporter, requiring excitation with electromagnetic radiation in the near-UV range, which is potentially damaging to living cells.

Consequently, significant effort has been expended to produce variant mutated forms of GFP with properties more suitable for use as an intracellular reporter.

A number of mutated forms of GFP with altered spectral properties have been described. A variant-GFP (Heim et al. (1994) Proc.Natl.Acad.Sci. 91, 12501) contains a Y66H mutation which blue-shifts the excitation and emission spectrum of the protein. However, this protein is only weakly fluorescent and requires potentially damaging Lw excitation.

A further mutant of GFP (Heim et al, Nature, (1995), 373, 663–664) contains a S65T mutation which red-shifts the optimum excitation and emission wavelengths relative to wtGFP and which is 4–6 fold brighter than wtGFP when expressed as a recombinant protein at 25° C. However, this variant does not yield bright fluorescence when expressed in hosts cultured at 37° C.

Ehrig et al (FEBS Lett., (1995), 367,163–6) describe two mutations of GFP, T203I and E222G, which individually delete one of the excitation maxima of wtGFP. The E222G mutation deletes the near-UV excitation peak at 395 nm and produces a red-shift in the excitation peak at 475 nm to 481 nm. The emission peak for this mutant protein is at 506 nm.

WO96/27675 describes two variant GFPs, obtained by random mutagenesis and subsequent selection for brightness, which contain the mutations V163A and V163A+S175G, respectively. These variants were shown to produce more efficient expression in plant cells relative to wtGFP and to increase the thermotolerance of protein folding. The double mutant V163A+S175G was observed to be brighter than the variant containing the single V163A mutant alone; however this mutant exhibits an undesirable blue-shifted excitation peak.

A further mutant, termed cycle-3, generated by molecular evolution through DNA shuffling (Crameri, A. et al, Nature Biotechnology, (1996), 14, 315–9) is available commercially from Invitrogen Inc. Cycle-3-GFP contains three mutations (F99S+M153T+V163A) which increase whole cell fluorescence approximately 42 fold when compared with wtGFP. However, this mutant retains the near-UV excitation maximum of the wtGFP, making it less suitable as a reporter for use in living cells.

The above mutations effectively address some of the spectral deficiencies of wtGFP as a biological reporter in providing variant forms of GFP which are compatible with lower energy excitation and which emit at wavelengths compatible with detection instrumentation commonly in use for measuring biological reporters. However, such mutations do not address the problem of inefficient folding and chromophore formation when wtGFP or spectral variants are expressed in hosts requiring growth at temperatures significantly greater than ambient.

U.S. Pat. No. 6,172,188 describes variant GFPs wherein the amino acid in position 1 preceding the chromophore has been mutated to provide an increase of fluorescence intensity. Such mutations include F64I, F64V, F64A, F64G and F64L, with F64L being the preferred mutation. These mutants result in a substantial increase in the intensity of fluorescence of GFP without shifting the excitation and emission maxima. F64L-GFP has been shown to yield an approximate 6-fold increase in fluorescence at 37° C. due to shorter chromophore maturation time.

In addition to the single mutants or randomly derived combinations of mutations described above, a variety of mutant-GFPs have been created which contain two or more mutations deliberately selected from those described above and other mutations, and which seek to combine the advantageous properties of the individual mutations to produce a protein with expression and spectral properties which are suited to use as a sensitive biological reporter in mammalian cells.

One mutant, commonly termed EGFP, available commercially from Clontech Inc., contains the mutations F64L and S65T (Cormack, B. P. et al, Gene, (1996), 173, 33–38). These mutations when combined, confer an approximate 35-fold increase in brightness over wtGFP and the spectral characteristics permit excitation and detection of EGFP with commonly used fluorescein excitation (488 nm) and emission filters (505 nm–530 nm). EGFP has been optimised for expression in mammalian systems, having been constructed with preferred mammalian codons.

U.S. Pat. No. 6,194,548 discloses GFPs with improved fluorescence and folding characteristics at 37° C. that contain, at least, the changes F64L and V163A and S175G. A further mutant GFP containing the F64L, S65T and V163A mutations has been described (Cubitt, A. B. et al, Methods in Cell Biology, (1999), 58, 19–29).

U.S. Pat. No. 6,077,707 describes a blue fluorescent protein (BFP) containing the F64L mutation in combination with Y66H and U.S. Pat. No. 6,194,548 describes a further BFP containing the F64L, Y66H, Y145F and L236R substitutions.

SUMMARY OF THE INVENTION

In view of the needs of the prior art, the present invention provides novel engineered derivatives of green fluorescent protein (GFP) which have an amino acid sequence which is modified by amino acid substitution compared with the amino acid sequence of wild type Green Fluorescent Protein. The modified GFPs exhibit enhanced fluorescence relative to wtGFP when expressed in non-homologous cells at temperatures above 30° C., and when excited at about 490 nm compared to the parent proteins, i.e. wtGFP. An example of a preferred protein is F64L-S175G-E222G-GFP. The modified GFPs provide a means for detecting GFP reporters in mammalian cells at lower levels of expression and/or increased sensitivity relative to wtGFP. This greatly improves the usefulness of fluorescent proteins in studying cellular functions in living cells.

The present invention provides a fluorescent protein which is derived from Green Fluorescent Protein (GFP), or any functional GFP analogue, and has an amino acid sequence which is modified by amino acid substitution as compared with the amino acid sequence of wild type Green Fluorescent Protein. The modified fluorescent protein includes an amino acid substitution at position F64, a single amino acid substitution at either position S65 or position E222, and an amino acid substitution at position S175 whereby the modified GFP has a different excitation spectrum and/or emission spectrum compared with wild type GFP.

Additionally, the present invention provides a fluorescent protein derived from Green Fluorescent Protein (GFP) and having the amino acid sequence as set forth in SEQ ID NO: 3 of FIG. 3.

The present invention also provides a fluorescent protein derived from Green Fluorescent Protein (GFP) and having the amino acid sequence as set forth in SEQ ID NO: 4 of FIG. 4.

The present invention further provides a nucleic acid molecule comprising a nucleotide sequence encoding a fluorescent protein which is derived from Green Fluorescent Protein (GFP), or any functional GFP analogue, and has an amino acid sequence which is modified by amino acid substitution compared with the amino acid sequence of wild type Green Fluorescent Protein. The modified fluorescent protein includes an amino acid substitution at position F64, a single amino acid substitution at either position S65 or position E222, and an amino acid substitution at position S175 wherein the modified GFP has a different excitation spectrum and/or emission spectrum compared with wild type GFP.

The present invention also further provides a method of measuring the expression of a protein of interest in a cell. The method includes the steps of i) introducing into a cell a nucleic acid molecule comprising a nucleotide sequence encoding a fluorescent protein which is derived from Green Fluorescent Protein (GFP), or any functional GFP analogue, according to the present invention. The nucleic acid molecule is operably linked to and under the control of an expression control sequence which moderates expression of said protein of interest; ii) culturing the cell under conditions suitable for the expression of the protein of interest; and iii) detecting the fluorescence emission of the Green Fluorescent Protein (GFP) or a functional GFP analogue as a means of measuring the expression of the protein of interest.

The present invention still further provides a method of determining the cellular and/or extracellular localisation of a protein of interest. The method includes the steps of i) introducing into a cell a nucleic acid molecule having a nucleotide sequence encoding a fluorescent protein which is derived from Green Fluorescent Protein (GFP), or any functional GFP analogue, according to the present invention and fused to a nucleotide sequence encoding a protein of interest. The nucleic acid molecule is operably linked to and under the control of a suitable expression control sequence; ii) culturing the cell under conditions suitable for the expression of the protein of interest; and iii) determining the cellular and/or extracellular localisation of the protein of interest by detecting the fluorescence emission by optical means.

The present invention even still further provides a method of comparing the effect of one or more test substance(s) on the expression and/or localisation of one or more different protein(s) of interest in a cell. The method includes the steps of i) introducing into a cell a nucleic acid molecule comprising a nucleotide sequence encoding a Green Fluorescent Protein (GFP) or a functional GFP analogue according to the present invention and optionally fused to a nucleotide sequence encoding a first protein of interest, where the nucleic acid molecule is operably linked to and under the control of a first expression control sequence; ii) culturing the cells under conditions suitable for the expression of the protein(s) of interest in the presence and absence of the test substance(s); iii) determining the expression and/or localisation of the protein(s) of interest in the cells by detecting the fluorescence emission by optical means; and iv) comparing the fluorescence emission obtained in the presence and absence of the test substance(s) to determine the effect of the test substance(s) on the expression and/or localisation of the protein(s) of interest. The introducing step may also include at least one different nucleic acid molecule encoding a protein reporter molecule optionally fused to a different protein of interest where each nucleic acid molecule is operably linked to and under the control of a second expression control sequence wherein the protein reporter molecule has or is capable of generating an emission signal which is spectrally distinct from that of the Green Fluorescent Protein (GFP) or functional GFP analogue.

BRIEF DESCRIPTION OF THE DRAWINGS

FIG. 1 is the nucleotide Sequence of wtGFP (Chalfie et al, Science, (1994), 263, 802–5) and referred to herein as SEQ ID NO: 1.

FIG. 2 is the corresponding amino acid sequence of wtGFP (Chalfie et al, Science, (1994), 263, 802–5) and referred to herein as SEQ ID NO: 2.

FIG. 3 is the predicted amino acid sequence of F64L-S175G-E222G-GFP and referred to herein as SEQ ID NO: 3.

FIG. 4 is the predicted amino acid sequence of F64L-S65T-S175G-GFP and referred to herein as SEQ ID NO: 4.

DETAILED DESCRIPTION OF THE PREFERRED EMBODIMENTS

Figure 5:
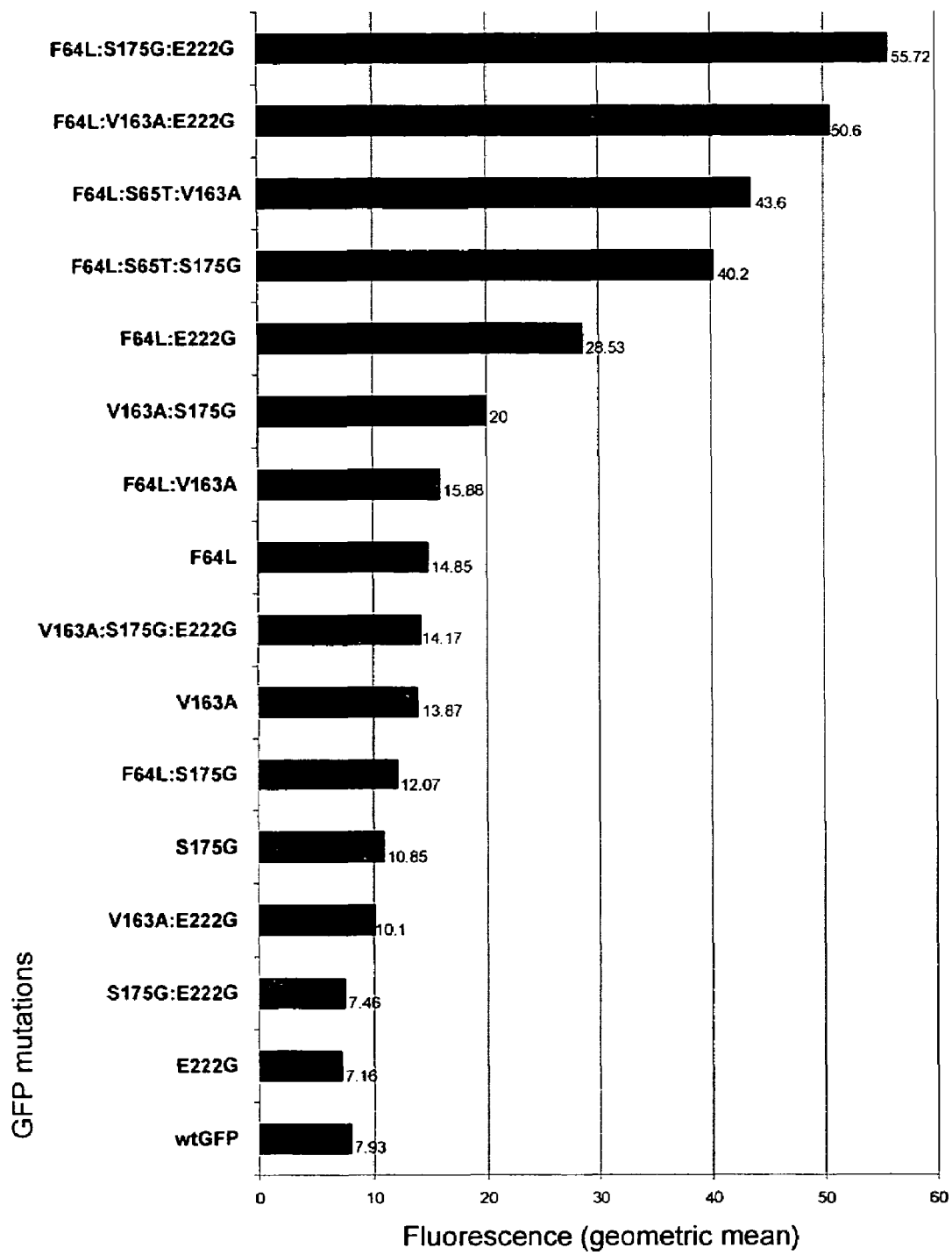
FIG. 5 is a plot showing average fluorescence intensities of mutant GFPs according to the invention.

The present invention provides novel engineered derivatives of green fluorescent protein (GFP) which exhibit enhanced fluorescence relative to wtGFP when expressed in non-homologous cells at temperatures above 30° C., and when excited at about 490 nm compared to the parent proteins, i.e. wtGFP. Mutant GFPs according to the invention provide a means for detecting GFP reporters in mammalian cells at lower levels of expression and/or increased sensitivity relative to wtGFP. This greatly improves the usefulness of fluorescent proteins in studying cellular functions in living cells. The multiply-mutated GFPs of this invention have fluorescence properties which are not predictable from the properties of the individual mutations when studied in isolation. Furthermore, it has surprisingly been found that certain GFPs according to the present invention, which do not contain any mutations in the chromophore region relative to wtGFP, exhibit enhanced fluorescence compared with mutant GFPs described previously.

In a first aspect of the invention, there is provided a fluorescent protein which is derived from Green Fluorescent Protein (GFP) or any functional GFP analogue and has an amino acid sequence which is modified by amino acid substitution compared with the amino acid sequence of wild type Green Fluorescent Protein said modified fluorescent protein comprising:
 i) an amino acid substitution at position F64;
 ii) a single amino acid substitution at a position selected from the group consisting of positions S65 and E222; and
 iii) an amino acid substitution at position S175;
 wherein the modified GFP has a different excitation spectrum and/or emission spectrum compared with wild type GFP.

Suitably, the amino acid F at position 64 may be substituted by an amino acid selected from the group consisting of Leu, Ile, Val, Ala and Gly, thereby providing F64L, F64I, F64V, F64A, or F64G substitutions. In a preferred embodiment of the first aspect, the amino acid Phe is substituted by Leu at position 64.

Suitably, the amino acid S at position 175 may be substituted by an amino acid selected from the group consisting of Gly, Ala, Leu, Ile and Thr, thereby providing S175G, S175A, S175L, S175I and S175T substitutions. In a preferred embodiment of the first aspect, the amino acid Ser is substituted by Gly at position 175.

In embodiments where the amino acid S at position 65 is substituted, it is suitably substituted by an amino acid selected from the group consisting of Gly, Ala, Leu, Cys, Val, Ile and Thr, thereby providing S65G, S65A, S65L, S65C, S65V, S65I or S65T substitutions. Preferably, the amino acid substitution at position 65 is the S65T substitution.

In embodiments where the amino acid Glu at position 222 is substituted, it is suitably substituted by an amino acid selected from the group consisting of Gly, Ala, Val, Leu, Ile, Phe, Ser, Thr, Asn and Gln, thereby providing E222G, E222A, E222V, E222L, E222I, E222F, E222S, E222T, E222N or E222Q substitutions. Preferably, the amino acid substitution at position 222 is the E222G substitution.

Suitably, the novel fluorescent proteins exhibit high fluorescence in cells expressing them when said cells are incubated at a temperature of 30° C. or above, preferably at a temperature of from 32° C. to 39° C., more preferably from 35° C. to 38° C. and most preferably at a temperature of about 37° C.

Preferably, the fluorescent protein according to the first aspect has an amino acid sequence which is modified by amino acid substitution compared with the amino acid sequence of wild type Green Fluorescent Protein having the sequence: SEQ ID NO: 2.

A preferred protein according to the present invention is a protein in which, in relation to SEQ ID NO: 2 of GFP, the amino acid Phe at position 64 has been substituted by Leu, the amino acid Ser at position 175 has been substituted by Gly and the amino acid Glu at position 222 has been substituted by Gly, and is shown herein as having the amino acid sequence as set forth in SEQ ID NO: 3.

An alternative preferred protein according to the present invention is a protein in which, in relation to SEQ ID NO: 2 of GFP, the amino acid Phe at position 64 has been substituted by Leu, the amino acid Ser at position 65 has been substituted by Thr and the amino acid Ser at position 175 has been substituted by Gly, and is shown herein as having the amino acid sequence as set forth in SEQ ID NO: 4.

Suitably, the GFP or functional GFP-analogue used to derive the fluorescent protein may be obtained from any convenient source. For example, native GFP derived from species of the genus Aequorea, suitably *Aequorea victoria*. The chromophore in wtGFP from *Aequorea victoria* is at positions 65–67 of the predicted primary amino acid sequence (SEQ ID NO: 2). In a preferred embodiment, the GFP is derived from *Aequorea victoria*.

The modified proteins of the present invention may be produced by introducing mutations in a sequence of the nucleic acid that encodes the protein. As used herein, a preferred sequence of the gene encoding WtGFP is derived from *Aequorea victoria*, published by Chalfie et al, (Science, (1994), 263, 802–5) disclosed as SEQ ID NO: 1 (FIG. 1). The corresponding amino acid sequence is shown in SEQ ID NO: 2 (FIG. 2). Alternative sequences of the GFP gene may be used, for example, the nucleotide (and predicted amino acid) sequences of the GFP gene described by Prasher et al, (Gene (1992), 111, 229) and the sequences as disclosed in WO 97/11094. In addition, alternative gene sequences that encode the fluorescent protein may incorporate a consensus Kozak nucleotide sequence (Kozak, M., Cell (1986), 44, 283), or preferred mammalian codons, to provide improved translation in mammalian systems. The nucleotide sequence corresponding to the fluorescent protein may also encode useful restriction enzyme sites and additional elements such as target sites for enzymes and purification tags. Methods for incorporation of a Kozak region, preferred mammalian codons, restriction enzyme sites, enzyme sites and purification tags are well known in the art and may result in the incorporation of amino acid residues and a change in numbering of amino acid residues in the fluorescent protein relative to the wtGFP numbering in the sequence provided.

Herein, the abbreviations used for the amino acids are those stated in J. Biol. Chem., (1968), 243, 3558.

In a second aspect of the invention, there is provided a fusion compound comprising a protein of interest fused to a fluorescent protein which is derived from Green Fluorescent Protein (GFP) or any functional GFP analogue and has an amino acid sequence which is modified by amino acid substitution compared with the amino acid sequence of wild type Green Fluorescent Protein said modified fluorescent protein comprising:
 i) an amino acid substitution at position F64;
 ii) a single amino acid substitution at a position selected from the group consisting of positions S65 and E222; and
 iii) an amino acid substitution at position S175;
 wherein said modified GFP has a different excitation spectrum and/or emission spectrum compared with wild type GFP.

In the context of the present invention, the term "protein of interest" is intended also to encompass polypeptides and peptide fragments. Examples of such proteins of interest include: NFκB and subunits thereof, RAC1, PLC domains, MAPKAP2, PKC, Cytochrome C, RHO, β-actin, STAT6, protein kinase C isotypes, LAMP1/2 TGN, ATP7A TGN and GLUT4.

In a third aspect of the present invention there is provided a nucleic acid molecule comprising a nucleotide sequence encoding a fluorescent protein which is derived from Green Fluorescent Protein (GFP) or any functional GFP analogue and has an amino acid sequence which is modified by amino acid substitution compared with the amino acid sequence of wild type Green Fluorescent Protein said modified fluorescent protein comprising:

i) an amino acid substitution at position F64;
ii) a single amino acid substitution at a position selected from the group consisting of positions S65 and E222; and
iii) an amino acid substitution at position S175;
wherein said modified GFP has a different excitation spectrum and/or emission spectrum compared with wild type GFP.

Preferably, the nucleic acid molecule according to the third aspect encodes a fluorescent protein having an amino acid sequence which is modified by amino acid substitution compared with the amino acid sequence of wild type Green Fluorescent Protein having the sequence: SEQ ID NO: 2.

In a particular embodiment of the third aspect, the nucleic acid molecule comprises a nucleotide sequence encoding a fluorescent protein derived from Green Fluorescent Protein (GFP) or any functional GFP analogue according to the invention fused to a nucleotide sequence encoding a protein of interest.

Preferably, the nucleic acid molecule is a construct comprising a DNA sequence.

Preferably, the nucleic acid molecule encodes a fluorescent protein having an amino acid sequence selected from the group consisting of SEQ ID NO: 3 and SEQ ID NO: 4.

As is well known, a single amino acid may be encoded by more than one nucleotide codon and thus each of the above nucleotide sequences may be modified to produce an alternative nucleotide sequence that encodes the same peptide. Thus, the preferred embodiments of the invention include alternative DNA sequences that encode the preferred proteins as previously described. It is to be understood that the preferred proteins (and the nucleic acid sequences from which they are derived), may include additional residues, particularly N- and C-terminal amino acids, or 5'- or 3'-nucleotide sequences, and still be essentially as described herein.

Suitably, the DNA construct encoding the novel fluorescent proteins may be prepared synthetically by established methods, e.g. the phosphoramidite method described by Beaucage and Caruthers, (Tetrahedron Letters (1981), 22, 1859–1869), or the method described by Matthes et al., (EMBO Journal (1984), 3, 801–805). According to the phosphoramidite method, oligonucleotides are synthesized, e.g. in an automatic DNA synthesizer, purified, annealed, ligated and cloned into suitable vectors.

The DNA construct encoding the fluorescent protein may also be prepared by recombinant DNA methodology, for example cDNA cloning. See for example, Sambrook, J. et al (1989) Molecular Cloning—A Laboratory Manual, Cold Spring Harbor Laboratory Press.

The DNA construct may also be prepared by polymerase chain reaction (PCR™) using specific primers, for instance as described in U.S. Pat. No. 4,683,202 or Saiki et al (Science (1988), 239, 487–491). A recent review of PCR™ (polymerase chain reaction methods may be found in PCR Protocols, (1990), Academic Press, San Diego, Calif., USA.

The gene sequence encoding the fluorescent protein may be joined in-frame with a gene encoding the protein of interest and the desired fusion protein produced when inserted into an appropriate expression vector. For example, polymerase chain reaction or complementary oligonucleotides may be employed to engineer a polynucleotide sequence corresponding to the fluorescent protein, 5' or 3' to the gene sequence corresponding to the protein of interest. Alternatively, the same techniques may be used to engineer a polynucleotide sequence corresponding to the fluorescent protein sequence 5' or 3' to the multiple cloning site of an expression vector prior to insertion of a gene sequence encoding the protein of interest. The polynucleotide sequence corresponding to the fluorescent protein sequence may comprise additional nucleotide sequences to include cloning sites, linkers, transcription and translation initiation and/or termination signals, labelling and purification tags.

In a fourth aspect, there is provided an expression vector comprising suitable expression control sequences operably linked to a nucleic acid molecule according to the present invention. The DNA construct of the invention may be inserted into a recombinant vector, which may be any vector that may conveniently be subjected to recombinant DNA procedures. The choice of vector will often depend on the host cell into which it is to be introduced. Thus, the vector may be an autonomously replicating vector, ie. a vector which exists as an extrachromosomal entity, the replication of which is independent of chromosomal replication, eg. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding a fluorescent protein of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the fluorescent protein of the invention.

The promoter may be any DNA sequence which shows transcriptional activity in a suitable host cell of choice, (eg. a bacterial cell, a mammalian cell, a yeast cell, or an insect cell) for expressing a fluorescent protein. The promoter may be derived from genes encoding proteins either homologous or heterologous to the host cell.

Examples of suitable promoters for directing the transcription of the DNA sequence encoding the fluorescent protein of the invention in mammalian cells are the CMV promoter (U.S. Pat. Nos. 5,168,062, 5,385,839), Ubiquitin C promoter (Wulff, M. et al., FEBS Lett. (1990), 261, 101–105), SV40 promoter (Subramani et al., Mol. Cell Biol. (1981), 1, 854–864) and MT-1 (metallothionein gene) promoter (Palmiter et al., Science (1983), 222, 809–814). An example of a suitable promoter for use in insect cells is the polyhedrin promoter (U.S. Pat. No. 4,745,051; Vasuvedan et al., FEBS Lett., (1992) 311, 7–11). Examples of suitable promoters for use in yeast host cells include promoters from yeast glycolytic genes (Hitzeman et al., J. Biol. Chem., (1980), 255, 12073–12080; Alber and Kawasaki, J. Mol. Appl. Gen., (1982), 1, 419–434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4c (Russell et al., Nature, (1983), 304, 652–654) promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gene, or the *Bacillus pumilus* xylosidase gene, or the phage Lambda PR or PL promoters or the *Escherichia coli* lac, trp or tac promoters.

The DNA sequence encoding the novel fluorescent proteins of the invention may also, if necessary, be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) terminators. The vector may further comprise elements such as polyadenylation signals (e.g. from SV40 or the adenovirus 5 E1b region), transcriptional enhancer sequences (e.g. the SV40 enhancer) and translational enhancer sequences (e.g. the ones encoding adenovirus VA RNAs).

The vector may further comprise a DNA sequence enabling internal ribosomal entry and expression of two proteins from one bicistronic transcript mRNA molecule. For example, the internal ribosomal entry sequence from the encephalomyocarditis virus (Rees S, et al, BioTechniques (1996), 20, 102–110 and U.S. Pat. No. 4,937,190).

The recombinant vector may further comprise a DNA sequence enabling the vector to replicate in the host cell in question. An example of such a sequence (when the host cell is a mammalian cell) is the SV40 origin of replication.

When the host cell is a yeast cell, examples of suitable sequences enabling the vector to replicate are the yeast plasmid 2µ replication genes REP 1–3 and origin of replication.

The vector may also comprise selectable markers, such as a gene that confers resistance to a drug, e.g. ampicillin, kanamycin, tetracyclin, chloramphenicol, puromycin, neomycin or hygromycin.

The procedures used to ligate the DNA sequences coding for the fluorescent protein of the invention, the promoter and optionally the terminator and/or targeting sequence, respectively, and to insert them into suitable vectors containing the information necessary for replication, are well known to persons skilled in the art (eg. Sambrook et al., op.cit.).

In a fifth aspect of the invention, there is provided a host cell transformed or transfected with a DNA construct comprising an expression vector according to the present invention.

The DNA construct or the recombinant vector of the invention is suitably introduced into a host cell which may be any cell which is capable of expressing the present DNA construct and includes bacteria, yeast and higher eukaryotic cells (Unger, T. F., The Scientist (1997), 11(17), 20–23; Smith, C., The Scientist (1998), 12(22): 20; Smith, C., The Scientist (1998), 12(3), 18; Fernandez, J. M. & Hoeffler, J. P., Gene Expression Systems—using nature for the art of expression, Academic Press 1999).

Examples of bacterial host cells which, on cultivation, are capable of expressing the DNA construct of the invention are Gram-positive bacteria, eg. species of *Bacillus* or Gram-negative bacteria such as *E. Coli*. The transformation of the bacteria may be effected by using competent cells in a manner known per se (cf. Sambrook et al., supra).

Examples of suitable mammalian cell lines are the HEK293 and the HeLa cell lines, primary cells, and the COS (e.g. ATCC CRL 1650), BHK (eg. ATCC CRL 1632, ATCC CCL 10), CHL (e.g. ATCC CCL39) or CHO (eg. ATCC CCL 61) cell lines. Methods of transfecting mammalian cells and expressing DNA sequences introduced in the cells are described in eg. Kaufman and Sharp, J. Mol. Biol., (1982), 159, 601–621; Southern and Berg, J. Mol. Appl. Genet., (1982), 1, 327–341; Loyter et al., Proc. Natl. Acad. Sci. USA, (1982), 79, 422–426; Wigler et al., Cell, (1978), 14, 725; Corsaro and Pearson, Somatic Cell Genetics, (1981), 7, 603, Graham and van der Eb, Virology (1973), 52, 456; and Neumann et al., EMBO J., (1982), 1, 841–845.

Examples of suitable yeast cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the fluorescent protein of the invention may be preceded by a signal sequence and optionally a leader sequence, e.g. as described above. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., J. Gen. Microbiol., (1986), 132, 3459–3465; U.S. Pat. No. 4,882, 279).

Transformation of insect cells and production of heterologous polypeptides therein may be performed as described in U.S. Pat. Nos. 4,745,051; 4,879,236; 5,155,037; 5,162, 222; EP 397485, all of which are incorporated herein by reference. The insect cell line used as the host may suitably be a *Lepidoptera* cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

In a sixth aspect, the invention provides a method for preparing a Green Fluorescent Protein (GFP) or a functional GFP analogue according to the present invention, the method comprising cultivating a host cell transformed or transfected with a nucleotide sequence according to the invention and obtaining therefrom the polypeptide expressed by said nucleotide sequence.

Suitably, the transformed or transfected host cells as described above are cultured in a suitable nutrient medium under conditions permitting the expression of a DNA construct according to the invention, after which the cells may be used in the screening method of the invention. Alternatively, the cells may be disrupted after which cell extracts and/or supernatants may be analysed for fluorescence and/or used to purify the GFP or functional GFP analogue of the invention.

The medium used to culture the cells may be any conventional medium suitable for growing the host cells, such as minimal or complex media containing appropriate supplements. Suitable media are available from commercial suppliers or may be prepared according to published protocols (eg. in catalogues of the American Type Culture Collection; Sambrook et al., supra).

For example, a fusion protein comprising glutathione S-transferase (GST) and GFP can be constructed and expressed in *E. coli*. The GFP may be joined in-frame to the C-terminus of GST in a pGEX plasmid vector (Amersham Pharmacia Biotech). Recombinant production of the fusion protein is carried out utilising a standard *E. coli* expression host, followed by purification employing glutathione affinity chromatography and removal of the GST tag by proteolytic cleavage.

In a seventh aspect of the present invention, there is provided a method of measuring the expression of a protein of interest in a cell. The method comprises:
  i) introducing into a cell a nucleic acid molecule comprising a nucleotide sequence encoding a fluorescent protein which is derived from Green Fluorescent Protein (GFP) or any functional GFP analogue according to the present invention said nucleic acid molecule being operably linked to and under the control of an expression control sequence which moderates expression of said protein of interest;
  ii) culturing the cell under conditions suitable for the expression of the protein of interest; and
  iii) detecting the fluorescence emission of the Green Fluorescent Protein (GFP) or a functional GFP analogue as a means of measuring the expression of the protein of interest.

In an eighth aspect of the present invention, there is provided a method of determining the cellular and/or extracellular localisation of a protein of interest which method comprises:
  i) introducing into a cell a nucleic acid molecule comprising a nucleotide sequence encoding a Green Fluorescent Protein (GFP) or a functional GFP analogue according to the invention fused to a nucleotide sequence encoding a protein of interest, said nucleic acid molecule being operably linked to and under the control of a suitable expression control sequence;
  ii) culturing said cell under conditions suitable for the expression of said protein of interest; and
  iii) determining the cellular and/or extracellular localisation of said protein of interest by detecting the fluorescence emission by optical means.

The fluorescent proteins of the present invention may also be used in a method to detect and compare the effect of a test substance on the regulation of expression and/or translocation of two or more different proteins of interest in a cell. Alternatively, they may be used in a method to compare the expression of a protein of interest and the simultaneous activity of an expression control sequence in response to a test substance. The fluorescent proteins may also be used in a method to compare the activity of two or more expression control sequences in a cell in response to a test substance. Such methods may be performed in the presence and in the absence of a test substance whose effect on the process is to be measured. For example, one detectable reporter molecule may be used as an internal reference and another as a variable marker, since regulated expression of a gene can be monitored quantitatively by fusion of an expression control sequence to a DNA construct encoding, eg. F64L-S175G-E222G-GFP, measuring the fluorescence, and normalising it to the fluorescence of a constitutively expressed spectrally distinct fluorescent molecule. The constitutively expressed spectrally distinct fluorescent molecule, for example BFP, acts as an internal reference.

Thus, in a ninth aspect of the present invention, there is provided a method of comparing the effect of one or more test substance(s) on the expression and/or localisation of one or more different protein(s) of interest in a cell which method comprises:
  i) introducing into a cell:
    a) a nucleic acid molecule comprising a nucleotide sequence encoding a Green Fluorescent Protein (GFP) or a functional GFP analogue according to the invention optionally fused to a nucleotide sequence encoding a first protein of interest, said nucleic acid molecule being operably linked to and under the control of a first expression control sequence; and optionally,
    b) at least one different nucleic acid molecule encoding a protein reporter molecule optionally fused to a different protein of interest, each said nucleic acid molecule being operably linked to and under the control of a second expression control sequence wherein said protein reporter molecule has or is capable of generating an emission signal which is spectrally distinct from that of said Green Fluorescent Protein (GFP) or a functional GFP analogue;
  ii) culturing said cells under conditions suitable for the expression of said protein(s) of interest in the presence and absence of said test substance(s);
  iii) determining the expression and/or localisation of said protein(s) of interest in said cells by detecting the fluorescence emission by optical means; and
  iv) comparing the fluorescence emission obtained in the presence and absence of said test substance(s) to determine the effect of said test substance(s) on the expression and/or localisation of said protein(s) of interest.

In a preferred embodiment of the ninth aspect, samples of said cells in a fluid medium are introduced into separate vessels for each of said test substances to be studied.

Preferably, the first and second expression control sequences are different.

Suitably, the protein reporter molecule may be selected from the group consisting of fluorescent proteins and enzymes. Preferred fluorescent proteins are those which have a spectrally distinguishable emission wavelength compared with the emission wavelength of the fluorescent proteins according to the present invention, for example, BFP. Suitable enzyme reporters are those which are suitable for generating a detectable (eg. a luminescent or fluorescent) signal in a substrate. Suitable enzyme/substrates include: luciferase/luciferin; β-galactosidase/DDAO galactoside; β-galactosidase/fluorescein di-β-D-galactopyranoside; alkaline phosphatase/Attophos.

In the methods of the invention, the fluorescence of cells transformed or transfected with the DNA construct according to the invention may suitably be measured by optical means in for example; a spectrophotometer, a fluorimeter, a fluorescence microscope, a cooled charge-coupled device (CCD) imager (such as a scanning imager or an area imager), a fluorescence activated cell sorter, a confocal microscope or a scanning confocal device, where the spectral properties of the cells in culture may be determined as scans of light excitation and emission.

The fluorescent proteins of the present invention have many additional applications, for example:
  i) Use as a non-toxic marker for selection of transfected cells containing an expression vector encoding at least the fluorescent protein of the invention. The fluorescence emission may be used to isolate transfected cells thereby overcoming the need for selection with toxic molecules such as antibiotics.

ii) Use as a protein label in living and fixed cells. The novel proteins exhibit strong fluorescence and are a suitable label for proteins present at low concentrations. Since no substrate is needed and visualization of the fluorescent protein does not damage the cells, dynamic analysis can be performed.

iii) Use as a marker in cell or organelle fusion. By labelling one or more cells or organelles with the novel proteins, for example, F64L-S175G-E222G-GFP, and other cells or organelles with same or another fluor, fusions such as heterokaryon formation can be monitored.

iv) Translocation of proteins fused to the novel proteins of the invention can be visualised. The translocation of intracellular proteins to a specific organelle can be visualised by fusing the protein of interest to a fluorescent protein, for example, F64L-S175G-E222G-GFP and labelling the organelle with another fluorescent molecule, eg. fluorescent protein. Translocation can then be detected as a spectral shift in the fluorescent proteins in the specific organelle.

v) Use as a secretion marker. By fusion of a fluorescent protein of the invention to a signal peptide or a peptide to be secreted, secretion may be followed in living cells.

vi) Use as genetic reporter or protein tag in transgenic animals. Due to the strong fluorescence of the novel proteins, they are suitable as tags for proteins and gene expression, since the signal to noise ratio is significantly improved over the prior art proteins, such as wild-type GFP.

vii) Use as a cell or organelle integrity marker. By expressing the novel proteins targeted to an organelle, it is possible to calculate the leakage of the protein and use that as a measure of cell integrity.

viii) Use as a transfection marker, and as a marker to be used in combination with FACS sorting (eg. as described in Example 3). Due to the increased brightness of the novel proteins the quality of cell detection and sorting can be significantly improved.

ix) Use as real-time probe working at near physiological concentrations.

Since the novel proteins of the present invention are significantly brighter than wtGFP when expressed in cells at about 37° C. and excited with light at about 490 nm, the concentration needed for visualization can be lowered. Target sites for enzymes engineered into the novel proteins, for example F64L-S175G-E222G-GFP, can therefore be present in the cell at low concentrations in living cells. This is important for two reasons: i) the probe must interfere as little as possible with the intracellular process being studied; and ii) the translational and transcriptional apparatus should be stressed minimally.

x) Transposon vector mutagenesis can be performed using the novel proteins as markers in transcriptional and translational fusions. Transposons may be used in microorganisms encoding the novel proteins. The transposons may be constructed for translational and transcriptional fusion to be used for screening for promoters. Transposon vectors encoding the novel proteins, for example F64L-S175G-E222G-GFP, can be used for tagging plasmids and chromosomes.

xi) Use as a reporter for bacterial detection by introducing the novel proteins into the genome of bacteriophages. By engineering the novel proteins, for example F64L-S175G-E222G-GFP, into the genome of a phage a diagnostic tool can be designed. F64L-S175G-E222G-GFP will be expressed only upon transfection of the genome into a living host. The host specificity is defined by the bacteriophage.

EXAMPLES

1. Cloning of GFP Gene and Template Vector Construction

The GFP gene used in the present study was contained within the plasmid pGFP (Chalfie et at., Science, (1994) 263 802–805; GenBank accession number U17997) obtained from Clontech Laboratories Inc. (Palo Alto, Calif., USA). The gene was amplified by PCR™ (polymerase chain reaction) using Pfu polymerase (Promega, Madison, Wis., USA) according to recognised protocols (Saiki et at., Science, (1988), 239, 487–491). The sequences of primers used were:

| | |
|---|---|
| GFP-1 5'-ggtacgggccgccaccatgagtaaaggagaagaacttttcac | SEQ ID No. 5 |
| GFP-2 5'-ggtacgggttaaccggttttgtatagttcatccatg | SEQ ID No. 6 |
| GFP-3 5'-ggtacgggccgccaccatgggatccaaaggagaagaacttttcac | SEQ ID No. 7 |

Primer GFP-1 exhibits homology to the 5' region of the GFP gene and contains a partial Kozak site (Kozak, M, Cell, (1986), 44, 283) prior to the start codon for efficient initiation of translation in mammalian systems. Primer GFP-2 exhibits homology to the 3' region of the GFP gene and contains an additional AgeI restriction enzyme site immediately prior to the stop codon to facilitate cloning of proteins by fusion to the C-terminus of GFP. Primer GFP-3 is similar to primer GFP-1 exhibiting homology to the 5' region of the GFP gene, but contains an additional restriction site (BamHI) immediately after the initiation codon to facilitate cloning of proteins by fusion to the N-terminus of GFP. Amplified products resulting from PCR™ (polymerase chain reaction) reactions containing primers GFP-1 and GFP-2, and GFP-3 and GFP-2 were tailed with a single 3'-deoxyadenosine using Taq polymerase (Amersham Pharmacia Biotech, Amersham, UK) and ligated into the TA cloning vector pTARGET (Promega) according to manufacturer's instructions. The correct orientation relative to the CMV promoter and sequence of the insert was determined by automated DNA sequencing.

2. Generation of Mutants of GFP

The following mutants of GFP were generated in the present study: F64L-GFP, V163A-GFP, S175G-GFP, E222G-GFP, F64L-E222G-GFP, F64L-V163A-GFP, F64L-S175G-GFP, V163A-S175G-GFP, V163A-E222G-GFP, S175G-E222G-GFP, F64L-S175G-E222G-GFP, V163A-S175G-E222G-GFP, F64L-V163A-E222G-GFP, F64L-S65T-S175G-GFP, F64L-S65T-V163A-GFP. Mutants of the GFP gene SEQ ID NO: 3) construct within pTARGET (See Example 1) were generated using the QuikChange™ site-directed mutagenesis kit (Stratagene, La Jolla, Calif., USA) according to manufacturer's instructions. The sequences of primers used to generate F64L, S65T, V163A, S175G and E222G single mutants have been documented in Table 1. Multiply-mutated GFP molecules were generated through successive mutagenesis reactions. All GFP mutant sequences were verified by automated sequencing.

pGEX-6P1 (Amersham Pharmacia Biotech). *E. coli* JM109 cells (Promega) containing an expression vector with the GST-GFP gene fusion were grown at 30° C. to an $OD_{600}$=0.6 in 2×YT broth containing 100 µg/ml ampicillin. Protein expression was induced with IPTG (0.1 mM) and incubation

TABLE 1

| Primer | Mutation | Sequence (5'—3') | SEQ ID NO. |
|---|---|---|---|
| GFP-64f | F64L | ccaacacttgtcactactctctcttatggtgttcaat | 8 |
| GFP-64r | F64L | attgaacaccataagagagagtagtgacaagtgttgg | 9 |
| GFP-65f | S65T | ccaacacttgtcactactctcacctatggtgttcaatgcttttca | 10 |
| GFP-65r | S65T | tgaaaagcattgaacaccataggtgagagtagtgacaagtgttgg | 11 |
| GFP-163f | V163A | gacaaacaaaagaatggaatcaaagccaacttcaaaattagacac | 12 |
| GFP-163r | V163A | gtgtctaattttgaagttggctttgattccattcttttgtttgtc | 13 |
| GFP-175f | S175G | caacattgaagatggaggcgttcaactagcagacc | 14 |
| GFP-175r | S175G | ggtctgctagttgaacgcctccatcttcaatgttg | 15 |
| GFP-222f | E222G | ccacatggtccttcttggctttgtaacagctgctgg | 16 |
| GFP-222r | E222G | ccagcagctgttacaaagccaagaaggaccatgtgg | 17 |

3. Influence of Individual Mutations and Combinations of F64L, S65T, V163A. S175G and E222G Mutations Upon GFP When Expressed in Mammalian Cells Plasmid DNA to be used for transfection was prepared for all GFP and EGFP constructs using the HiSpeed plasmid purification kit (Qiagen, Westberg, NL). DNA was diluted to 100 ng. µl-1 in 18-Megohm water (Sigma) and 1 µg used for transfections. For 50–80% confluency on the day of transfection, HeLa cells were plated at a density of $5 \times 10^4$/well in 6-well plates and incubated overnight. A 1:3 (1 µg:3 µl) ratio of DNA to FuGene6 reagent (Roche) was used for each transient transfection reaction; 3 µl FuGene6 was added to 87 µl serum-free DMEM medium (Sigma) (containing penicillin/streptomycin, L-glutamine (GibcoBRL) and gently tapped to mix, then 10 µl (1 µg) construct DNA was added and again gently mixed. The FuGene6:DNA complex was incubated at room temperature for 40 minutes then added dropwise directly to the cells without changing the medium, and the plates swirled for even distribution.

Fluorescence measurements were made 24 or 48 hours after transfection. Briefly, the cells were washed in phosphate-buffered saline, released with the addition of 2 drops of Trypsin (GibcoBRL) and resuspended in 1 ml of complete DMEM medium (containing penicillin/streptomycin, L-glutamine and foetal bovine serum (Sigma). The cells were vortexed and analysed on a FACS Calibur flow cytometer (Becton Dickinson & Co., NJ, USA) for characterisation of whole cell fluorescence, with excitation at 488 nm and emission viewed with fluorescence filter set 530/30 nm (range 515–545 nm). 10,000 events were collected for each transfection and 6–10 replicates carried out for each construct. Average fluorescent intensities from the FACS analysis were obtained as geometric means (mean fluorescence on log scale) and are shown in FIG. 5.

4. Purification of Fluorescent Proteins From *E. Coli*

The gene for the mutant F64L-S175G-E222G-GFP (Example 2) was excised from pTARGET with BamHI and SaiI and sub-cloned into the IPTG-inducible, GST-fusion vector continued for 16 hours. Cells were pelleted by centrifugation, resuspended in PBS and lysed by sonication (four 10 second bursts at 20 µm with intermittent cooling on ice). Cellular debris was removed by centrifugation and the lysate containing soluble GST-GFP fusion protein was purified using glutathione sepharose columns (Amersham Pharmacia Biotech). Protein was then exchanged and eluted in PBS using a PD10 column (Amersham Pharmacia Biotech). The presence of a single band of correct molecular weight in the protein preparation was confirmed by SDS-PAGE using 4–12% Bis-TRIS® HCL (hydroxymethyl) aminomethane hydrochloride buffered polyacrylamide gel sold under the trademark NuPAGE by Invitrogen. To assess protein concentration and purity, the protein preparation was subjected, in duplicate, to acid hydrolysis and filtration before amino acid analysis by ion exchange chromatography using a Pharmacia alpha plus series II analyser.

The extinction coefficient (Table 2) was determined on a UV/vis spectrometer (Unicam). Quantum yield (Table 2) was determined according to the method documented by Patterson et al (Biophysical Journal, (1997), 73 2782–2790). Samples of equal optical density at respective absorbance maxima were prepared, and diluted, in 10 mM TRIS® HCL (hydroxymethyl) aminomethane hydrochloride pH 8 for the purified GFP preparation and a fluorescein reference standard (Molecular Probes). Fluorescence emission was measured in the region 490–600 nm using a LS50B luminescence spectrometer (Perkin Elmer) and results for the GFP preparation were compared directly to those for the fluorescein standard (QY=85).

TABLE 2

| Protein | Absorbance peak (nm) | Extinction coefficient ($M^{-1} cm^{-1}$) | Emission peak (nm) | QY |
|---|---|---|---|---|
| F64L-S175G-E222G-GFP | 481 | 46213* | 506 | 0.6* |

*Mean of two measurements

Figure 6:
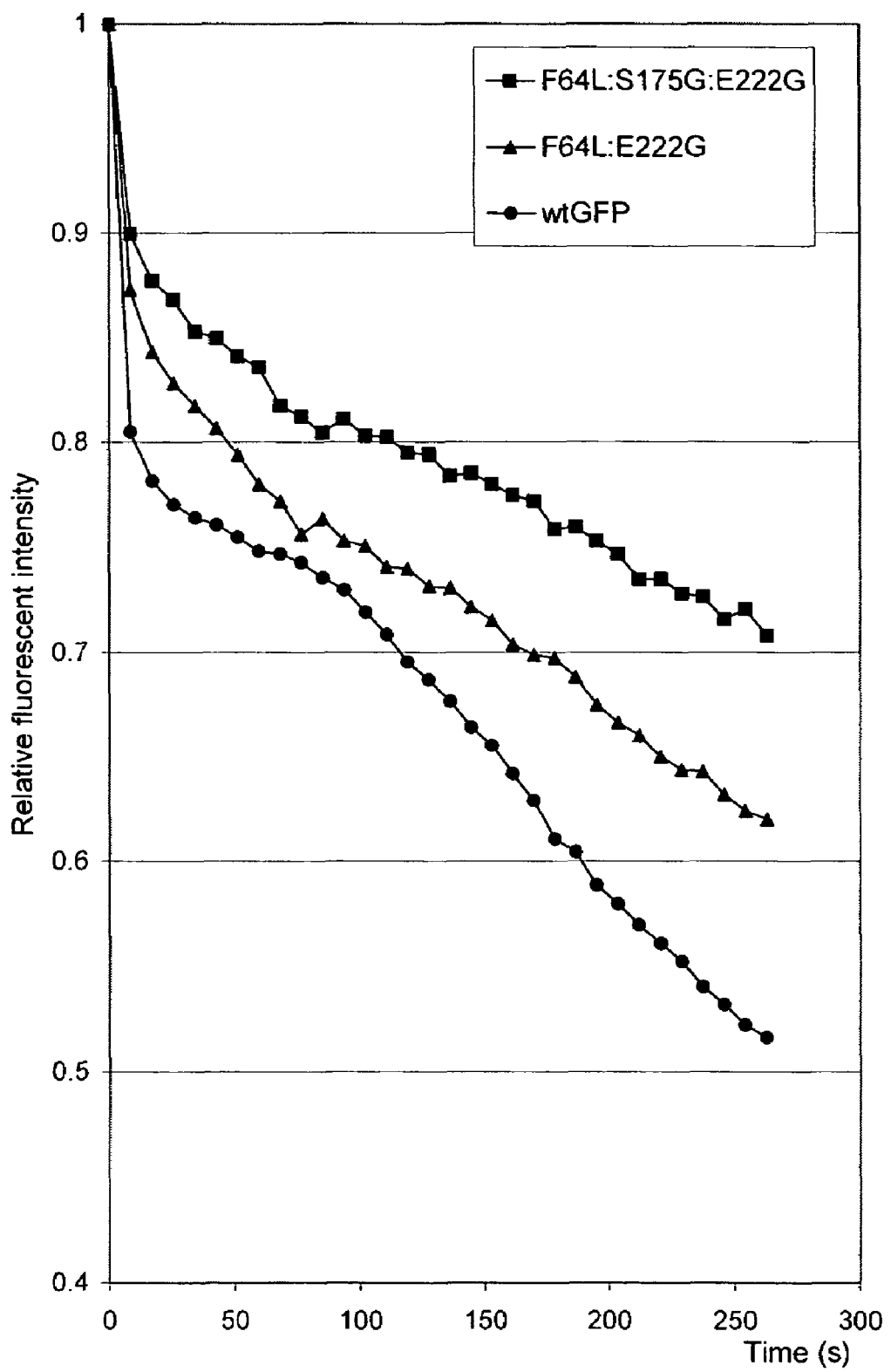
FIG. 6 is a plot showing relative photodegradation of mutant GFPs according to the invention.

To evaluate the degree of photodegradation of the mutants F64L-S175G-E222G-GFP and F64L-E222G relative to wtGFP, 50 ng of DNA was transfected into HeLa cells according to the method outlined in Example 3. For 50–80% confluency on the day of transfection, HeLa cells were plated at a density of 5×10³/well in a ViewPlate™-96 (Packard, Meriden Conn., USA). Twenty-four hours after transfection, the cells were imaged live on a LEADseeker™ Cell Analysis System (Amersham Pharmacia Biotech) and bleached at high laser power (19.94 mW) with a 488 nm Argon laser (emission filter 535–45 nm). Thirty-two individual images were taken over 260s with non-continuous illumination and all fluorescent proteins showed marked photodegradation as shown in FIG. 6.

5. Measurement of NFκB Translocation

NFκB is an activator of transcription and a component of signalling pathways which are responsive to a variety of inducers including cytokines, lymphokines, and some immunosuppressive agents.

The human NFκB P65 subunit gene (GenBank Accession number: M62399) was amplified using PCR™ (polymerase chain reaction) according to recognised protocols (Saiki et al., Science, (1988), 239, 487–491). The sequences of primers used were:

```
NFκB-1
5'-ttttactcgagatggacgaactgttccccctca   SEQ ID No. 18

NFκB-2
5'-ttttgaagcttggagctgatctgactcagcagg   SEQ ID No. 19
```

The P65 subunit was fused to the N terminus of GFP (SEQ ID NO: 3) in the vector pCORON1000 (Amersham Pharmacia Biotech), under the control of a CMV promoter. This was transfected into CHO-hir cells using FuGene6 reagent (Roche) and standard transfection procedures and a stable cell line was produced containing the P65-GFP construct.

Figure 7:
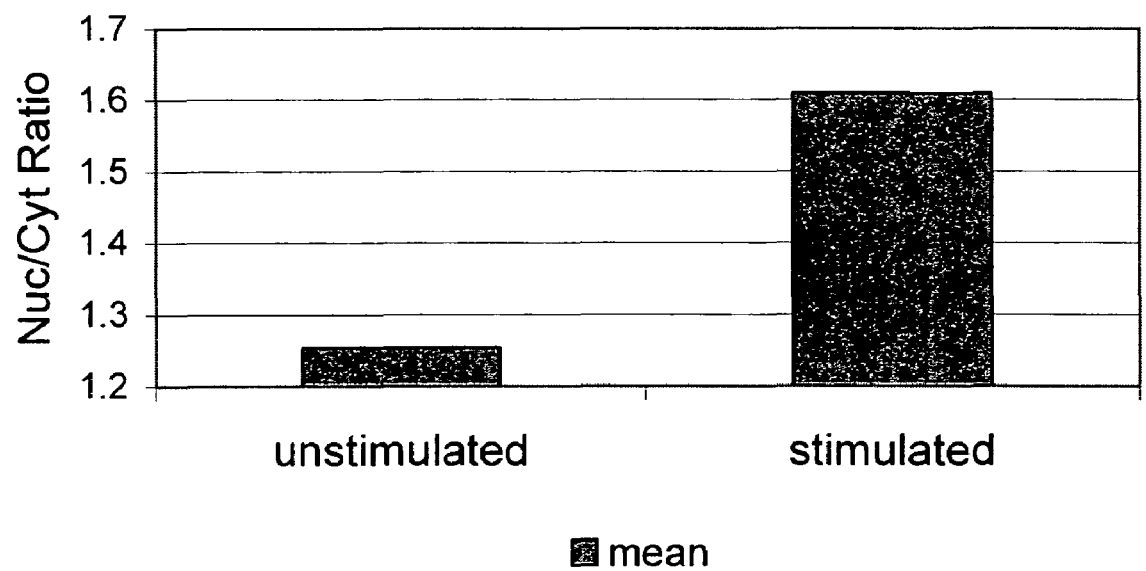
FIG. 7 is a plot demonstrating the increase in the ratio of nuclear to cytoplasmic fluorescence intensity on translocation of P65-GFP from the cytoplasm to the nucleus of CHO-hir cells following agonist addition.

CHO-hir, P65-GFP cells were seeded into 96 well microtitre plates at a confluency of 5×10³ cells/well in DMEM media (Sigma) containing penicillin/streptomycin, L-glutamine (GibcoBRL) and incubated overnight at 37° C. 1 hr before the assay was run, the media was removed and replaced with 100 μl serum free DMEM/well. 100 μl of 5 μM DRAQ5 (Biostatus) in Krebs buffer was added to each well and incubated for 15 minutes at 37° C. The plate was then placed in the imager (LEADseeker Cell Analysis System) and wells were imaged at varying time points following addition of agonist (50 μl of 40 ng/ml IL1β). Translocation of the P65-GFP was observed from the cytoplasm to the nucleus following agonist addition. The ratio of nuclear/cytoplasmic fluorescence is shown in FIG. 7.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

---

What is claimed is:

1. A modified Green Fluorescent Protein (GFP) having the amino acid sequence of SEQ ID NO:2 except for:
  i) an amino acid substitution at position F64;
  ii) a single amino acid substitution at a position selected from the group consisting of positions S65 and E222; and
  iii) an amino acid substitution at position S175;
wherein said modified GFP has a different excitation spectrum or a different emission spectrum compared with wild type GFP or has a different excitation spectrum and a different emission spectrum compared with wild type GFP.

2. The modified GFP of claim 1, wherein the amino acid Phe at position 64 has been substituted by an amino acid selected from the group consisting of Leu, Ile, Val, Ala and Gly.

3. The modified GFP of claim 1, wherein the amino acid Ser at position 175 has been substituted by an amino acid selected from the group consisting of Gly, Ala, Leu, Ile, and Thr.

4. The modified GFP of claim 1, wherein the amino acid Ser at position 65 has been substituted by an amino acid selected from the group consisting of Gly, Ala, Cys, Val, Ile, and Thr.

5. The modified GFP of claim 1, wherein the amino acid Glu at position 222 has been substituted by an amino acid selected from the group consisting of Gly, Ala, Val, Leu, Ile, Phe, Ser, Thr, Asn and Gln.

6. The modified GFP of claim 1, selected from F64L-S175G-E222G-GFP and F64L-S65T-S175G-GFP.

7. A modified Green Fluorescent Protein (GFP) having the amino acid sequence of SEQ ID NO:3 except for:
  i) an amino acid substitution at position F64L;
  ii) an amino acid substitution at position E222G; and
  iii) an amino acid substitution at position S175G;
wherein said modified GFP has a different excitation spectrum or a different emission spectrum compared with wild type GFP or has a different excitation spectrum and a different emission spectrum compared with wild type GFP.

8. A modified Green Fluorescent Protein (GFP) having the amino acid sequence of SEQ ID NO:4 except for:
  i) an amino acid substitution at position F64L;
  ii) an amino acid substitution at position S65T; and
  iii) an amino acid substitution at position S175G;
wherein said modified GFP has a different excitation spectrum or a different emission spectrum compared with wild type GFP or has a different excitation spectrum and a different emission spectrum compared with wild type GFP.

9. A fusion protein comprising a protein of interest fused to the modified GFP of claim 1.

* * * * *